United States Patent [19]

Christidis et al.

[11] Patent Number: 4,481,374

[45] Date of Patent: Nov. 6, 1984

[54] PROCESS FOR THE PREPARATION OF HYDROXYBENZALDEHYDES

[75] Inventors: Yani Christidis; Jean-Claude Vallejos, both of Paris, France

[73] Assignee: Societe Francaise Hoechst, Puteaux, France

[21] Appl. No.: 414,243

[22] PCT Filed: Jan. 14, 1982

[86] PCT No.: PCT/FR82/00007

§ 371 Date: Aug. 26, 1982

§ 102(e) Date: Aug. 26, 1982

[87] PCT Pub. No.: WO82/02549

PCT Pub. Date: Aug. 5, 1982

[30] Foreign Application Priority Data

Jan. 20, 1981 [FR] France .............................. 81 00967

[51] Int. Cl.$^3$ .............................................. C07C 45/38
[52] U.S. Cl. .................................... 568/432; 562/459; 549/436
[58] Field of Search ................ 568/431, 432; 562/459; 549/436

[56] References Cited

U.S. PATENT DOCUMENTS 4,306,083  12/1981  Ma ...................................... 568/432
4,351,962   9/1982  Gradeff et al. ...................... 568/432

OTHER PUBLICATIONS

Claus et al., Monatshefte fur Chemie, vol. 103, No. 4, (1972), 1178–1193.

Primary Examiner—Bernard Helfin
Attorney, Agent, or Firm—Karl W. Flocks; Sheridan Neimark

[57] ABSTRACT

The invention relates to a process for the preparation of hydroxybenzaldehydes by oxidation of hydroxybenzylic alcohols through oxygen or oxygen-containing gas, said process being carried out in aqueous alkaline medium in the absence of any catalyst whatsoever, at a temperature comprised between 25° and 50° C. and in the presence of an alkaline hydroxide in such a quantity that the molar ratio of alkaline hydroxide to hydroxybenzylic alcohol used is comprised between 2.25 and 10.

9 Claims, No Drawings

PROCESS FOR THE PREPARATION OF HYDROXYBENZALDEHYDES

This invention relates to a novel process for the preparation of hydroxybenzaldehydes by the oxidation of primary hydroxybenzylic alcohols through oxygen or oxygen-containing gas in aqueous alkaline mediums.

In the prior art, very many processes either chemical or catalytic, have been proposed for oxidizing a benzylic alcohol to the corresponding benzaldehyde.

It is known particularly to oxidize a hydroxybenzylic alcohol either substituted or not, to the corresponding hydroxybenzaldehyde through catalytic oxidization by oxygen or oxygen-containing gases in aqueous alkaline mediums and in the presence of a metallic catalyst based on a noble metal such as platinum or palladium. To avoid the specific disadvantages of these processes such as the necessity of using large quantities of catalyst, the German patent application DE AS No. 1 188 069 (U.S. Pat. No. 3,321,526) teaches the use of boric acid as an activator of the palladium catalysts; other activators of this type of oxidation have been proposed, such as for example, according to the U.S. Pat. No. 3,673,257, the cadmium, cerium, indium, lanthanum, copper, yttrium, magnesium, uranyl, zinc, cadmium-tetramine ions, or to Japanese patent application No. 55-59128, an inorganic salt of a metal selected from the following metals: lead, bismuth, silver and tin.

Other processes have been described with a view to either reducing consumption of metal from the platinum group, or inhibiting secondary reactions, or finally, to preparing a specific aromatic aldehyde.

Thus, the French patent application No. 77-13941 (2 350 323) teaches the use of a catalyst based on a noble metal of the platinum group associated with lead, silver, tellurium and/or tin and/or their compounds, the French patent application No. 75-09932 (2 305 420) describes a co-catalyst based on a derivative of bismuth, the Japanese patent application No. 55-22615 discloses a process for oxidation of piperonylic alcohol to piperonal in the presence of a catalyst based on a metal of the platinum group associated with an inorganic salt of a metal selected among the following metals: lead, bismuth, silver and tin, and finally, the U.S. Pat. No. 4,190,605 realizes the acceleration of the catalytic oxidation by activation of the palladium based catalyst through preliminary reaction thereof with a hydroxybenzylic alcohol.

It is to be noted that in all of these processes the influence of the temperature is not negligible and may sometimes be determinant.

Also, it is known to realize catalytic oxidation of a hydroxybenzylic alcohol in the presence of an organic solvent. Thus again, the Japanese patent application No. 55-35003 teaches such an oxidation carried out either in the dimethylsulfoxide or in the dimethylformamide in the presence of a vanadium catalyst. Moreover, the temperature must be in the range of 100° to 180° C.

Thus, the oxidation processes of hydroxybenzylic alcohol to hydroxybenzaldehydes in aqueous alkaline medium through oxygen or oxygen-containing gases are catalytic processes requiring a metallic catalyst constituted either by a derivative of vanadium or by a metal of the platinum group alone or associated with various mineral ions. These expensive catalysts at the end of the reaction require expensive treatments for recovery and/or purification thereof thereby resulting in ineluctable losses, which therefore increase the manufacturing costs. Furthermore, keeping reactional temperatures which are often in excess of 50° C. implies not insignificant thermal energy consumptions which add to such costs.

The Applicant has now discovered in a completely unexpected manner a new process, which is the object of this invention, for the preparation of hydroxybenzaldehydes by oxidation of primary hydroxybenzylic alcohols by means of oxygen or oxygen-containing gas in an aqueous alkaline medium, characterized by effecting such oxidation at a temperature lower than, or equal to, 50° C., on the one hand, and on the other hand, in the absence of any catalyst whatsoever.

According to a characteristic of the invention, the aqueous alkaline medium consists of an aqueous solution of an alkaline hydroxide used in such a quantity that the molar ratio of hydroxide to hydroxybenzylic alcohol is in the range of 2.25 to 10.

According to an alternative, the aqueous alkaline medium can be admixed with an organic solvent inert under the reactional conditions and miscible with water.

According to another characteristic, the reactional medium may comprise an accelerator or a mixture of accelerators based on the following metals: copper, cobalt, iron and manganese.

More precisely, according to this alternative of the process, the accelerators susceptible to be used are metallic ions coming from oxides, or mineral or organic salts, whether anhydrous or hydrated, of copper, cobalt, iron and/or manganese, at various degrees of valence such as copper II sulfate, hexahydrated cobalt II chloride, iron III chloride, manganese II sulfate.

The process according to the invention has various advantages such as the realization of the oxidation in a homogeneous phase, the suppression of a catalyst based on a noble metal of the platinum group, the possibility of effecting oxidation in the absence of any catalyst whatsoever, or according to the alterntive of the process, in the presence of metallic accelerating ions at various degrees of valence, little expensive, mentioned heretofore; and finally, the possibility of working at temperatures that may not be higher than 50° C.

The quantities of accelerator(s) to be used according to the alternative of the process according to the invention, may be varied between large limits. The accelerating effect is already traceable with additions of 0.01 gram-equivalent of the metal or metallic compound per mole of hydroxybenzylic alcohol used. Usually, there is used from 0.01 to 0.5 gram-equivalent of the metal or metallic compound per mole of hydroxybenzylic alcohol used.

The process according to the invention is carried out in an aqueous alkaline medium, the alkaline medium being advantageously an alkaline hydroxide such as sodium hydroxide or potassium hydroxide. Generally, there is used more than one mole of alkaline agent per mole of hydroxybenzylic alcohol implemented. Advantageously, one operates with an excess equal to, or higher than, 2.25 moles of alkaline agent per mole of alcohol used, and the molar ratio of alkaline agent to the alcohol used is usually within the range of 2.25 to 10.

The concentration of hydroxybenzylic alcohol in the aqueous alkaline solution is selected generally so as to keep a solution throughout the oxidation reaction. Generally, a concentration by weight of hydroxybenzylic alcohol of between 5 and 40% is adopted. In certain particular cases wherein the starting alcohol should present very bad solubility in aqueous alkaline medium, there can be used a third water-miscible organic solvent inert under reactional conditions, such as a primary aliphatic $C_1$-$C_3$ alcohol, the dioxane, so as to obtain a solution. The nature and quantity of the solvent to be used in each specific case can be easily determined by a few preliminary tests.

For the realization of the process according to the invention, it is important that oxygen or the oxygen-containing gases should be in intimate contact with the aqueous alkaline solution containing the starting hydroxybenzylic alcohol, and possibly any accelerator(s). To this end, it is usually carried out under strong agitation, and a pressure of oxygen or the oxygen-containing gas higher than the ambient pressure.

Advantageously, this oxidation is effected under a pressure within the range of 2 to 10 bars. If desired, the development of the oxidation can be followed up from the quantity of oxygen absorbed, but most frequently, such absorption stops of itself or slows down very much when the theoretical quantity of oxygen required for forming the desired aldehyde was absorbed.

But, preferentially, the development of the reaction is followed up if necessary by physical analysis such as the analysis through the proton nuclear magnetic resonance NMR of a previously treated test sample.

The process according to the invention is usually carried out at a temperature lower than, or equal to, 50° C., and advantageously, at a temperature within the range of 25° to 50° C.

The primary hydroxybenzylic alcohols used as starting products correspond to the general formula I:

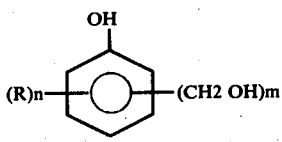

in which m is equal to 1 or 2 n is equal to 1, 2, 3, ... (5−m)

R, identical or different, represent a hydrogen atom, a halogen atom, an alkyl, aryl, alkoxy, hydroxy, methylenedioxy, carboxy group, or a condensed ring. The particularly preferred R substituents are alkyl, alkoxy, hydroxy or methylenedioxy groups.

The primary hydroxybenzylic alcohols of the general formula I are known or can be obtained by known means such as the addition of one or more moles of formaldehyde on a substituted phenol of the general formula II:

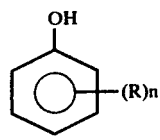

in which n is equal to 1, 2, 3, 4 and R has the meaning as mentioned hereinabove.

Another advantage of the process according to the invention is that it can be implemented at the start of raw hydroxybenzylic alcohols not purified containing among others various impurities resulting from their preparation, or else at the start of isomeric hydroxybenzylic mixtures of alcohols (constitution isomers). In the latter case, at the end of oxidation reaction one purifies the formed hydroxybenzaldehydes by known means such as water vapour entrainment, distillation, fractioned crystallization, chromatography.

One can also selectively oxidize one of the two hydroxymethyl groups to aldehyde thereby obtaining hydroxybenzaldehydes substituted among others by a hydroxymethyl group.

At the end of the reaction, the isolation of the desired hydroxybenzaldehyde is realized by acidification to a pH lower than, or equal to 3.5 of the reactional medium previously filtered if need be to eliminate any possible mechanical impurities, followed by a separation of the so released hydroxybenzaldehyde by means known in themselves such as filtration, extraction, water vapour entrainment. If necessary, the hydroxybenzaldehyde can thereafter be purified by known means such as recrystallization, distillation and so on.

The reaction times vary as a function of many factors, i.e. nature of the starting alcohols, agitation speed, reactional temperature, oxygen pressure or oxygen-containing gas pressure, accelerator concentration and alkaline agent concentration and so on, and they may vary within a large range, but are generally comprised between 1 hour and 48 hours.

The hydroxybenzaldehydes obtained according to the process of the invention are important intermediaries of organic synthesis and/or precious materials for obtaining aromas or perfumes.

The following examples are for illustration of the process according to the invention, but do not limit it in any way.

EXAMPLES 1 TO 3

There is heated at 50° C. for 24 hours under agitation of 1000 revolutions per minute, and with oxygen pressure of P bars, a solution of:

0.63 mole (78.2 g) of parahydroxybenzylic alcohol, HBA, a moles (y g) of sodium hydroxide in pellets in 300 g of water.

At the end of the reaction, the cooled reactional medium brought to the ambient temperature is diluted with water, then acidified to pH=3 with concentrated hydrochloric acid filtered if necessary to eliminate mechanical impurities, and finally, submitted to repeated extractions with ethyl acetate. The organic extraction phases united are thereafter washed with water, dried on anhydrous magnesium sulfate, filtered and dry concentrated under vacuum at a temperature lower than, or equal to 30° C. Thus, there is isolated b grams of a mixture of starting alcohol and parahydroxybenzaldehyde, PHB, in form of oil, the relative proportions of which are determined by nuclear magnetic resonance, NMR, in solution in deuterated chloroform.

In the following table I there are mentioned the various factors of these examples as well as the yields R, the conversion rates T, and the selectivities S. The yield R is the number of aldehyde moles formed, divided by the number of alcohol moles implemented, multiplied by one hundred. The conversion rate T is the ratio of the number of alcohol moles consumed, divided by the number of alcohol moles used, multiplied by one hundred. The selectivity S is the ratio of the number of aldehyde moles formed to the number of alcohol moles consumed, multiplied by one hundred. These three parameters are related by the relation:

$$R = S.T. \frac{1}{100}$$

TABLE I

| Ex. No | NaOH moles a | NaOH grams y | Molar ratio NaOH/alcohol | Pressure O₂ in bars p | Gross Weight in g b | Mass % aldehyde PHB | Mass % alcohol HBA | S % | T % | R % |
|---|---|---|---|---|---|---|---|---|---|---|
| 1 | 2.88 | 115.2 | 4.6 | 8 | 34.5 | 61.9 | 38.1 | 33.4 | 83 | 27.8 |
| 2 | 1 | 40 | 1.6 | 8 | 59.4 | 10 | 90 | 24.5 | 31.7 | 7.8 |
| 3 | 5.76 | 230.4 | 9.1 | 8 | 72.5 | 57 | 43 | 88.9 | 60.3 | 53.6 |

EXAMPLES 4 TO 8

There is heated at 50° C. for 24 hours under an agitation of 1000 revolutions per minute and under a pressure of 8 bars of oxygen a mixture of:

0.63 mole (78.2 g) of parahydroxybenzylic alcohol,
2.88 moles (115.2 g) of sodium hydroxide in pellets,
c moles (x grams) of a metallic salt selected among the following salts: pentahydrated cupric sulfate, hexahydrated cobalt II chloride, hexahydrated ferric chloride, heptahydrated nickel II sulfate, tetrahydrated manganese II sulfate in 300 g of water. Thereafter, one operates according to example 1. The results obtained are recorded in Table II.

The molar ratio of metallic salt to parahydroxybenzylic alcohol is 0.0127.

EXAMPLES 9 TO 16

There is heated at 8° C. for t hours under an agitation of 1000 revolutions per minute, and under a pressure of P bars of oxygen, a solution of:

0.63 mole (78.2 g) of parahydroxybenzylic alcohol,
a moles (y g) of sodium hydroxide in pellets,
c moles (z g) of pentahydrated cupric sulfate in n grams of water.

Thereafter, one operates according to example 1. The results obtained are recorded in table III.

TABLE III

| Ex No | NaOH a moles | NaOH y g | Water n in g | CuSO₄, 5H₂O moles c | CuSO₄, 5H₂O g z | Temperature θ° C. | Duration t hrs. | Pressure O₂ in bars p | Raw product Weight in g b | Mass % aldehyde PHB | Mass % alcohol HBA | S % | T % | R % |
|---|---|---|---|---|---|---|---|---|---|---|---|---|---|---|
| 9 | 1.62 | 64.8 | 300 | 0.046 | 11.4 | 50 | 8 | 8 | 49 | 94 | 6 | 62.2 | 96.2 | 59.8 |
| 10 | 2.88 | 115.2 | 300 | 0.046 | 11.4 | 50 | 24 | 8 | 74.7 | 100 | 0 | 97.7 | 100 | 97.7 |
| 11 | 1.62 | 64.8 | 300 | 0.008 | 2 | 50 | 24 | 8 | 69 | 100 | 0 | 89.8 | 100 | 89.8 |
| 12 | 1.62 | 64.8 | 300 | 0.046 | 11.4 | 50 | 8 | 2 | 73.5 | 92 | 8 | 94.3 | 92.5 | 87.3 |
| 13 | 1.62 | 64.8 | 300 | 0.004 | 1 | 50 | 8 | 8 | 55.3 | 92 | 8 | 70.2 | 94.3 | 66.7 |
| 14 | 1.42 | 56.8 | 235 | 0.0063 | 1.57 | 50 | 8 | 8 | 76.3 | 94 | 6 | 77.1 | 95.4 | 73.5 |
| 15 | 1.62 | 64.8 | 300 | 0.046 | 11.4 | 25 | 24 | 8 | 62.2 | 92 | 8 | 79.5 | 93.6 | 74.4 |
| 16 | 1.134 | 45.4 | 150 | 0.008 | 2 | 50 | 24 | 8 | 97.1 | 94 | 6 | 78.5 | 95.3 | 74.8 |

EXAMPLES 17 TO 19

The results mentioned in Table IV are obtained at the start of the orthohydroxybenzylic alcohol OHB (saligenol) and of vanillic alcohol VA, by practicing according to an operative mode similar to that described in example 1, under the reactional conditions mentioned in Table IV.

It is obvious that this invention was only described in a purely explanative and not at all limitative way, and that any useful modification can be brought thereto without departing from its scope such as defined in the following claims.

TABLE II

| Ex. no | Metallic salt moles | Metallic salt weight in g | Nature of metallic salt | Molar ratio of metallic salt to alcohol | Weight of raw product in g b | Mass % aldehyde PHB | Mass % alcohol HBA | S % | T % | R % |
|---|---|---|---|---|---|---|---|---|---|---|
| 4 | 0.008 | 2 | CuSO₄, 5H₂O | 0.0127 | 69.3 | 82.3 | 17.7 | 88.1 | 84 | 74.1 |
| 5 | 0.008 | 1.9 | CoCl₂, 6H₂O | 0.0127 | 64.4 | 100 | 0 | 83.8 | 100 | 83.8 |
| 6 | 0.008 | 2.2 | FeCl₃, 6H₂O | 0.0127 | 49.6 | 51.8 | 48.2 | 47.7 | 69.8 | 33.4 |
| 7 | 0.008 | 2.24 | NiSO₄, 7H₂O | 0.0127 | 34.2 | 56 | 44 | 30.8 | 80.9 | 24.9 |
| 8 | 0.008 | 1.8 | MnSO₄, 4H₂O | 0.0127 | 57.9 | 46.6 | 53.4 | 57.9 | 60.3 | 34.9 |

TABLE IV

| Ex. No | Nature of the alcohol | Weight of the alcohol | NaOH moles | NaOH g | Nature of the catalyst | Weight of the catalyst moles | Weight of the catalyst g | Water in g | T θ° C. | Duration t in hrs. | S % | T % | R % |
|---|---|---|---|---|---|---|---|---|---|---|---|---|---|
| 17 | OHB | 78.2 g 0.63 mole | 2.88 | 115.2 | CuSO₄, 5H₂O | 0.046 | 11.4 | 300 | 50 | 24 | 84.1 | 100 | 84.1 |
| 18 | OHB | 78.2 g 0.63 mole | 1.62 | 64.8 | CuSO₄, 5H₂O | 0.046 | 11.4 | 300 | 50 | 24 | 60.75 | 100 | 60.75 |
| 19 | VA | 97.1 g 0.63 mole | 1.62 | 64.8 | CuSO₄, 5H₂O | 0.008 | 2 | 300 | 50 | 7 | | | 58.3 |

OHB: orthohydroxybenzylic alcohol
VA: vanillic alcohol

We claim:

1. A process for the preparation of hydroxybenzaldehydes by oxidation, through oxygen or an oxygen-containing gas, of hydroxybenzylic alcohols of the general formula:

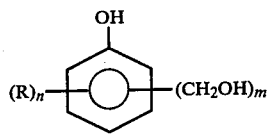

in which m is equal to 1 or 2; n is equal to the difference $5 - m$; and the rests R are identical or different, and each represents a hydrogen or halogen atom, or an alkyl, aryl, alkoxy, hydroxy, carboxy, or methylene-dioxy group, or a condensed ring, such process being carried out in a homogeneous aqueous alkaline phase in the absence of noble metal catalyst, at a temperature between 25° and 50° C., and in the presence of sodium or potassium hydroxide, in such quantity that the molar ratio of said hydroxide to hydroxy-benzylic alcohol implemented is between 2.25 and 10.

2. A process according to claim 1, wherein the pressure of oxygen or the oxygen-containing gas is higher than, or equal to 1 bar.

3. A process according to claim 1, wherein the reaction is accelerated by addition of a compound of a metal selected from the groups consisting of copper, cobalt, iron, manganese and mixtures of such compounds.

4. A process according to claim 3, wherein the molar ratio of the metallic compound to the starting hydroxybenzylic alcohol is between 0.01 and 0.1.

5. A process according to claim 1, wherein the reaction is carried out with a concentration of starting hydroxybenzylic alcohol comprised between 5 and 40% by weight.

6. A process according to claim 1, wherein the reaction is effected in the presence of ions selected from the group consisting of cupric, cobalt II ions, and their mixtures.

7. A process accordng to claim 1, wherein the reaction is effected in the presence of a water-miscible organic solvent inert under the reactional conditions.

8. A process according to claim 1, wherein the starting alcohol is parahydroxybenzylic alcohol whereby the parahydroxybenzaldehyde is obtained.

9. A process according to claim 1, wherein the starting alcohol is the orthohydroxybenzylic alcohol whereby the salicylic aldehyde is obtained.

* * * * *